US011395816B2

(12) United States Patent
Gros et al.

(10) Patent No.: US 11,395,816 B2
(45) Date of Patent: Jul. 26, 2022

(54) CORROLES FOR TREATING HUMAN CYTOMEGALOVIRUS INFECTIONS

(71) Applicant: UNIVERSITE DE BOURGOGNE, Dijon (FR)

(72) Inventors: Claude Gros, Neuilly les Dijon (FR); Franck Gallardo, Montauban (FR); Nicolas Desbois, Bessey les Citeaux (FR)

(73) Assignee: UNIVERSITE DE BOURGOGNE, Dijon (FR)

( * ) Notice: Subject to any disclaimer, the term of this patent is extended or adjusted under 35 U.S.C. 154(b) by 57 days.

(21) Appl. No.: 15/733,145

(22) PCT Filed: Nov. 27, 2018

(86) PCT No.: PCT/EP2018/082695
§ 371 (c)(1),
(2) Date: May 28, 2020

(87) PCT Pub. No.: WO2019/105928
PCT Pub. Date: Jun. 6, 2019

(65) Prior Publication Data
US 2021/0369671 A1 Dec. 2, 2021

(30) Foreign Application Priority Data
Nov. 29, 2017 (EP) .................... 17306655

(51) Int. Cl.
A61K 31/40 (2006.01)
A61K 31/409 (2006.01)
A61P 31/22 (2006.01)
A61K 31/444 (2006.01)
A61K 31/496 (2006.01)
A61K 31/522 (2006.01)
A61K 31/662 (2006.01)
A61K 31/675 (2006.01)

(52) U.S. Cl.
CPC .......... A61K 31/409 (2013.01); A61K 31/444 (2013.01); A61K 31/496 (2013.01); A61K 31/522 (2013.01); A61K 31/662 (2013.01); A61K 31/675 (2013.01); A61P 31/22 (2018.01)

(58) Field of Classification Search
CPC .............................. A61K 31/409; A61P 31/22
USPC ......................................................... 514/185
See application file for complete search history.

(56) References Cited

U.S. PATENT DOCUMENTS

2011/0098262 A1* 4/2011 Yondim ............... C07D 487/22
514/185
2011/0144078 A1* 6/2011 Gross ...................... A61P 9/00
514/185

OTHER PUBLICATIONS

International Search Report and Written Opinion, dated Mar. 14, 2019, from corresponding/related International Application No. PCT/EP2018/082695.
Darla M.B. Carvalho et al., "Antimicrobial photodynamic activity of porphyrin derivatives: potential application on medical and water disinfection", Journal of Porphyrins and Phthalocyanines, 2009, pp. 574-577, vol. 13.

(Continued)

Primary Examiner — Shengjun Wang
(74) Attorney, Agent, or Firm — Nixon & Vanderhye

(57) ABSTRACT

Disclosed is a family of corroles for its use in the treatment of an infection by human herpesvirus, especially in the treatment of an infection by human cytomegalovirus.

11 Claims, 4 Drawing Sheets

(56) References Cited

OTHER PUBLICATIONS

Claude P. Gros et al., "Synthesis and Antiviral Activity Evaluation of Nitroporphyrins and Nitrocorroles as Potential Agents against Human Cytomegalovirus Infection", ACS Infectious Diseases, 2015, pp. 350-356.
Daniel T. Gryko et al., "Refined methods for the synthesis of meso-substituted A3- and trans-A2B-corroles", Org. Biomol. Chem., 2003, pp. 350-357, vol. 1.
Karl M. Kadish et al., "Clarification of the Oxidation State of Cobalt Corroles in Heterogeneous and Homogeneous Catalytic Reduction of Dioxygen", Inorganic Chemistry, 2008, pp. 6726-6737, vol. 47.
Roberto Paolesse et al., "Synthesis and Functionalization of meso-Aryl-Substituted Corroles", J. Org. Chem., 2001, pp. 550-556, vol. 66.
Roel Straetemans et al., "Design and Analysis of Drug Combination Experiments", Biometrical Journal, 2005, pp. 299-308, vol. 47, No. 3.

\* cited by examiner

CORROLES FOR TREATING HUMAN CYTOMEGALOVIRUS INFECTIONS

BACKGROUND OF THE INVENTION

Field of the Invention

The present invention is related to a family of corroles for its use in the treatment of an infection by human cytomegalovirus.

Description of the Related Art

Human cytomegalovirus (hCMV) is a member of the Herpesviridae family that infect 60-80% of worldwide population.

Although primo-infection is generally silent or associated with a mononucleosic syndrome in immunocompetent people, it causes severe syndromes in immunocompromised persons (e.g., seroconversion during the first quarter of pregnancy or HIV positive people, for example).

As for all herpes viruses, after primary infection, the virus persists in a latent state lifelong in monocytes and CD34+ progenitors. Latent infection reactivates in outbreaks that depend on environmental factors, immune state, and stress level. hCMV spreads from person to person through body fluids, such as blood, saliva, urine, semen, and breast milk. hCMV is a common virus that infects people at any age. Most hCMV infections are silent, which means that the majority of people who are infected with hCMV have no signs or symptoms.

However, pregnant women who are infected during the first quarter of pregnancy can transmit hCMV to their foetus, sometimes causing a congenital hCMV infection. Congenital hCMV infection can cause problems from hearing loss to severe developmental and neuronal disabilities. In the US, hCMV infection is the first cause of congenital malformation.

Nowadays many previous vaccine approaches fail to provide complete protection against hCMV infection. Current anti-hCMV therapies include treatment with nucleoside analogues such as Cidofovir and Ganciclovir that inhibit virus replication by acting as fraudulent building blocks for viral DNA synthesis.

However, these drugs have adverse effects, such as myelosuppression or nephrotoxicity, and may lead to the emergence of antiviral-resistant hCMV strains during long-term or repeated treatments. Thus, the development of non-nucleoside hCMV inhibitors with novel mechanisms of action is an important focus area of antiviral research. The strategies for the design of new antiviral drugs must aim to develop more selective compounds with a broad spectrum of antiviral activity and little or no drug resistance induction.

Gros et al. (*Acs Infect. Dis.* 2015, 1, 350-356) reported on 2015 potential antiviral activity of nitrocorroles bearing nitro groups as substituents at the meta- or para-position of phenyl groups on position 5, 10 or 15 of corroles. However, it was observed that a nitrocorrole of type A3 was able to reduce the proportion of infected MRC5 cells only when added before infection. When this compound is added after hCMV adsorption and entry, it does not seem to have an impact on hCMV infection.

By the way, these nitrocorroles do not display a satisfactory selectivity index, that is to say the ratio between the cytotoxicity of a compound on cells without hCMV infection and the cytotoxicity of said compound on infected cells.

Taking these shortcomings in account, there is still a need to develop a new drug with unique mechanism of action (moA), being used in hCMV infection and having better selectivity index in the treatment of hCMV infection.

SUMMARY OF THE INVENTION

Against all expectations, the Inventors of the present invention have observed that a family of corroles bearing at least one fluorine atom as the substituent of groups on meso position 5, 10 or 15 of corroles can display an anti-hCMV activity in host cells after hCMV infection and a significantly better selectivity index.

The first subject-matter of the present invention is to provide a corrole of type A3 or A2B of formula (I):

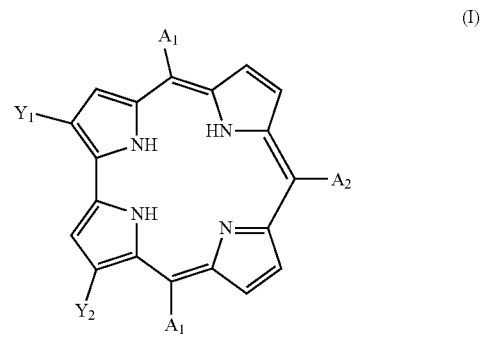

wherein $Y_1$ and $Y_2$ are identical or different and each independently chosen from —H, —$SO_3H$, —$SO_3^-$, —$NO_2$, —CHO, —$NH_2$, —$NH_3^+$, —COOH, —$COO^-$ $A_1$ and $A_2$ are identical or different and each independently represents a phenyl group of formula (II),

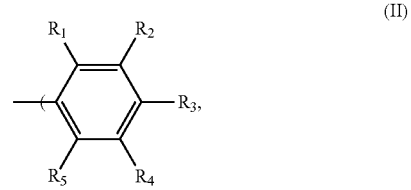

or a pyridinium group of formula (III)

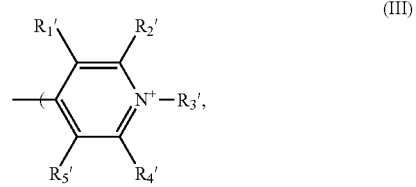

or
a five membered heterocycle of formula (IV)

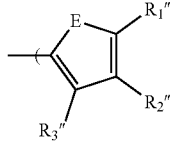

each of $R_1$, $R_2$, $R_3$, $R_4$ and $R_5$ of formula (II); each of $R_1'$, $R_2'$, $R_4'$ and $R_5'$ of formula (III); and each of $R_1''$, $R_2''$, and $R_3''$ of formula (IV) being chosen independently of each other from:
(a). —H, —CN, —NO$_2$, —CHO, —SO$_3$H, —OH, —SH, —C≡CH, —NH$_2$, —COOH, —CONH$_2$,
(b). a halogen atom, selected from a chlorine atom, a fluorine atom, a bromine atom, or an iodine atom,
(c). a (C$_1$-C$_8$) alkyl chain,
(d). a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
(e). —CX$_3$, X being a halogen atom selected from a chlorine atom, a fluorine atom, a bromine atom, or an iodine atom,
(f). —OR$_a$, —NR$_a$R$_b$, —NHR$_a$, —COOR$_a$, —CONHR$_a$, —CONR$_a$R$_b$, —SO$_3$R$_a$, —SO$_2$NHR$_a$, —COR$_a$, —SR$_a$, —C≡CR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$ wherein n is an integer chosen from 1, 2, 3, 4 or 5,
(g). a group of formula

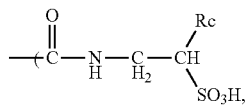

wherein R$_c$ is —COOH, or —SO$_3$H,
(h). a pyridinium group of formula

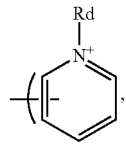

wherein R$_d$ is a (C$_1$-C$_8$) alkyl chain, or —(CH$_2$)$_n$SO$_3^-$, n being an integer chosen from 1, 2, 3, 4 or 5,
R$_3'$ of formula (III) being chosen from
—H, —CONH$_2$,
a (C$_1$-C$_5$) alkyl chain,
a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
a group —(CH$_2$)$_n$SO$_3^-$, n being an integer chosen from 1, 2, 3, 4 or 5
—OR$_a$, —NR$_a$R$_b$, —NHR$_a$, —COOR$_a$, —CONHR$_a$, —CONR$_a$R$_b$, —COR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$ wherein n is an integer chosen from 1, 2, 3, 4 or 5,
E of formula (IV) is chosen from —O—, —S—, —Se—, —NH—,
with the proviso that at least one of A$_1$ or A$_2$ bears at least one fluorine atom on position R$_1$, R$_2$, R$_3$, R$_4$, R$_5$, R$_1'$, R$_2'$, R$_4'$ or R$_5'$,
or a pharmaceutically acceptable salt thereof, or an optical isomer thereof, for its use in the treatment of an infection by human herpesvirus chosen from the group comprising cytomegalovirus, herpes simplex virus-1, herpes simplex virus-2, varicella zoster virus, epstein-barr virus, roseolovirus.

According to an embodiment, the present invention provides a corrole of formula (I) or a pharmaceutically acceptable salt thereof, or an optical isomer thereof, for its use in the treatment of an infection by human cytomegalovirus, such as Pneumonitis, esophagitis, gastritis, enterocolitis, retinitis, hepatitis, encephalitis causing by human CMV infection.

More particularly, the corroles of the present invention can be used in the treatment of an infection of human cytomegalovirus in an immunodeficient patient, such as HIV-infected patients, or a patient receiving organ transplant or in pregnant women.

According to in vitro trials carried out in human retinal cell culture, it is observed that a corrole of the present invention, even at low concentration, can significantly decrease hCMV infection level of cells and viral DNA accumulation level in infected cells. Moreover, the corroles of the present invention have better selectivity index than that of nitrocorroles previously described by Gros et al. (2015).

According to the invention, the term "a corrole of type A3" is meant to be a corrole wherein the A$_1$ and the A$_2$ are identical. In another word, a corrole of type A3 is a corrole wherein the three substituent groups on meso position 5, 10 and 15 of said corrole are identical.

According to the invention, the term "a corrole of type A2B" is meant to be a corrole wherein the A$_2$ is different from the A$_1$. In another word, a corrole of type A2B is a corrole wherein the substituent groups on meso position 5 and 15 are identical and they are different from the substituent group on meso position 10 of said corrole.

The term "a (C$_1$-C$_8$) alkyl chain" is meant to be a saturated straight or branched hydrocarbon chain containing from 1 to 8 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl.

The term "with the proviso that at least one of A$_1$ or A$_2$ bears at least one fluorine atom on position R$_1$, R$_2$, R$_3$, R$_4$, R$_5$, R$_1'$, R$_2'$, R$_4'$ or R$_5'$" means that:
when the corrole of the present invention is a corrole of type A3, each of A$_1$ and A$_2$ bears at least one fluorine atom on position R$_1$, R$_2$, R$_3$, R$_4$, or R$_5$, if A$_1$ and A$_2$ are a phenyl group of formula (II); or at least one fluorine atom on position R$_1'$, R$_2'$, R$_4'$ or R$_5'$ if A$_1$ and A$_2$ are a pyridinium of formula (III); or
when the corrole of the present invention is a corrole of type A2B, at least A$_1$ bears at least one fluorine atom on position R$_1$, R$_2$, R$_3$, R$_4$, or R$_5$ if A$_1$ is a phenyl group of formula (II), or on position R$_1'$, R$_2'$, R$_4'$ or R$_5'$ if A$_1$ is a pyridinium of formula (III); or
when the corrole of the present invention is a corrole of type A2B, at least A$_2$ bears at least one fluorine atom on position $R_1$, $R_2$, $R_3$, $R_4$, or $R_5$ if $A_2$ is a phenyl group of formula (II), or on position $R_1'$, $R_2'$, $R_4'$ or $R_5'$ if $A_2$ is a pyridinium of formula (III).

The term "pharmaceutically acceptable salt" refers to those salts which are, within the scope of sound medical judgment, suitable for use in contact with the tissues of humans without undue toxicity, irritation, allergic response and the like.

A pharmaceutically acceptable salt of a corrole of formula (I) of the present invention refers to salts which retain the biological effectiveness of corrole of formula (I) and are not biological undesirable for human.

According to the present invention, a pharmaceutically acceptable salt of a compound of the invention can be a pharmaceutically acceptable, organic or inorganic acid or base salt of a compound of the invention.

A pharmaceutically acceptable salt of a corrole of formula (I) can be obtained by reacting said corrole with a variety of organic and inorganic positive counter ions well known in the art, for example sodium, potassium, calcium, magnesium, ammonium, tetraalkylammonium, and the like. A pharmaceutically acceptable salt of a corrole of formula (I) can also be obtained by reacting said corrole with pharmaceutically acceptable acids. Specific examples include inorganic acid salts such as hydrochlorides and sulfates; and organic acid salts such as formates, trifluoroacetates, acetates, tartrates, maleates, fumarates, succinates and methanesulfonates.

The term "optical isomers" refers to molecules that differ three-dimensionally by the placement of substituents around one or more atoms in a molecule.

According to an embodiment of corroles of type A2B of the present invention, $A_1$ and $A_2$ are both phenyl groups of formula II which are substituted differently.

In another embodiment of corroles of type A2B of the present invention, $A_1$ and $A_2$ are both pyridinium groups of formula II which are substituted differently.

In an embodiment of the corrole of the present invention, when $A_1$, $A_2$ or $R_3'$ is a pyridinium group which does not bear a —$SO_3$ group, said corrole comprises a counter ion such as $Cl^-$, $Br^-$ or $I^-$.

According to an embodiment of the corroles of the present invention, the substituent groups $A_1$ and/or $A_2$ are represented by one of formula (II1), (II2), (II3), (III1), (III2), (IV1) or (IV2)

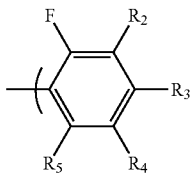
(II1)

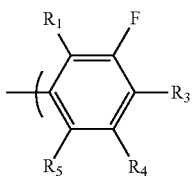
(II2)

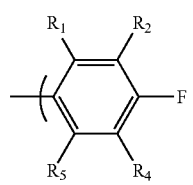
(II3)

-continued

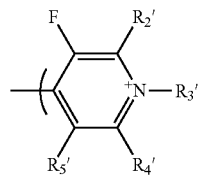
(III1)

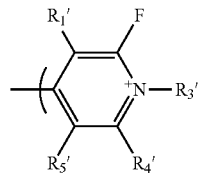
(III2)

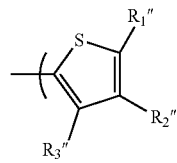
(IV1)

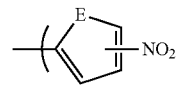
(IV2)

or a pharmaceutically acceptable salt thereof, or an optical isomer thereof.

In said formulas, the substituents $R_1$, $R_2$, $R_3$, $R_4$, $R_5$, $R_1'$, $R_2'$, $R_3'$, $R_4'$, $R_5'$, $R_1''$, $R_2''$, $R_3''$ and E are as defined above.

Thus in this embodiment at least one of $A_1$ and $A_2$ or both are selected from (II1), (II2), (II3), (III1), (III2), (IV1) or (IV2). $A_1$ and $A_2$ may be identical or different.

According to a more particular embodiment of the corroles of the present invention, $A_1$ and/or $A_2$ are represented by one formula chosen from formula (II4), formula (II5), formula (II6), formula (III3), formula (III4), formula (III5) or formula (IV3).

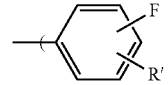
(II4)

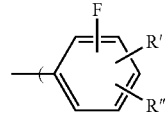
(II5)

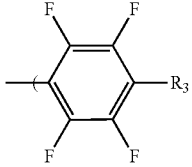
(II6)

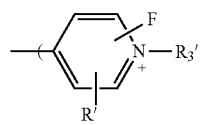
(III3)

-continued

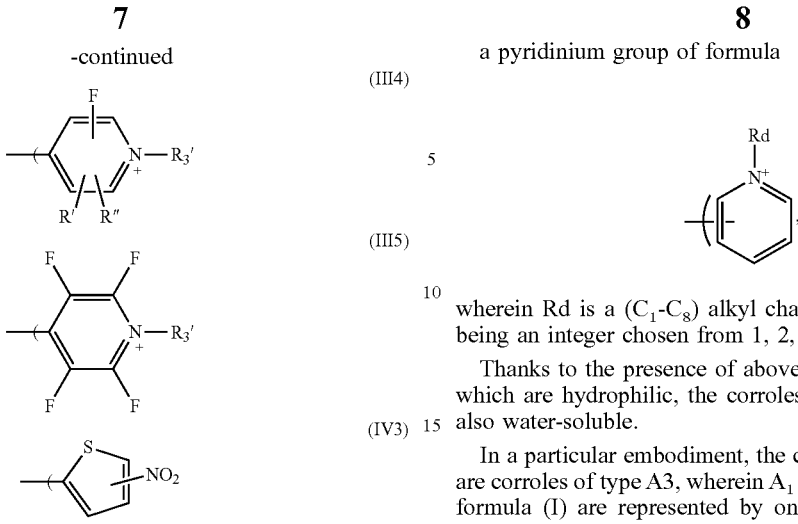

wherein R' and R" represent respectively two different substituents among $R_1$, $R_2$, $R_3$, $R_4$ and $R_5$ or two different substituents among $R_1'$, $R_2'$, $R_4'$ and $R_5'$; $R_1$, $R_2$, $R_3$, $R_4$, $R_5$, $R_1'$, $R_2'$, $R_3'$, $R_4'$, or $R_5'$ being defined as before.

According to formula (II4), the fluorine atom and R' represent two of $R_1$, $R_2$, $R_3$, $R_4$ or $R_5$, while the remaining three other substituents among $R_1$, $R_2$, $R_3$, $R_4$ or $R_5$ are hydrogen.

Thus for example, if F corresponds to $R_1$ and R' corresponds to $R_2$, then $R_3$, $R_4$ and $R_5$ are hydrogen.

According to formula (II5), the fluorine atom, R' and R" represent three of $R_1$, $R_2$, $R_3$, $R_4$ or $R_5$, while the remaining two other substituents among $R_1$, $R_2$, $R_3$, $R_4$ or $R_5$ are hydrogen.

Thus for example, if F, R' and R" respectively correspond to $R_1$, $R_2$ and $R_3$, then $R_4$ and $R_5$ are hydrogen.

According to formula (III3), the fluorine atom and R' represent two of $R_1'$, $R_2'$, $R_4'$ or $R_5'$, while the remaining two other substituents among $R_1'$, $R_2'$, $R_4'$ or $R_5'$ are hydrogen.

Thus for example, if F corresponds to $R_1'$ and R' corresponds to $R_2'$, then $R_4'$ and $R_5'$ are hydrogen.

According to formula (III4), the fluorine atom, R' and R" represent three of $R_1'$, $R_2'$, $R_4'$ or $R_5'$, while the reaming forth substituent among $R_1'$, $R_2'$, $R_4'$ or $R_5'$ is hydrogen.

Thus for example, if F, R' and R" respectively correspond to $R_1'$, $R_2'$ and $R_4'$, then $R_5'$ is a hydrogen.

Thus in this embodiment at least one of $A_1$ and $A_2$ or both are selected from formula (II4), formula (II5), formula (II6), formula (III3), formula (III4), formula (III5), or formula (IV3). $A_1$ and $A_2$ may be identical or different.

According to an embodiment of the corroles of the present invention, at least one of $A_1$ or $A_2$ bears at least one substituent, among $R_1$, $R_2$, $R_3$, $R_4$, or $R_5$ of formula (II) or among $R_1'$, $R_2'$, $R_4'$ or $R_5'$ of formula (III), or among $R_1''$, $R_2''$ or $R_3''$ of formula (IV) being chosen from:

a PEG chain of formula $-(CH_2-CH_2-O)_n-H$ or of formula $-(CH_2-CH_2-O)_n-CH_3$, wherein n is an integer chosen from 1, 2, 3, 4 or 5, a group of formula

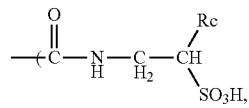

wherein Rc is $-COOH$, or $-SO_3H$, a pyridinium group of formula

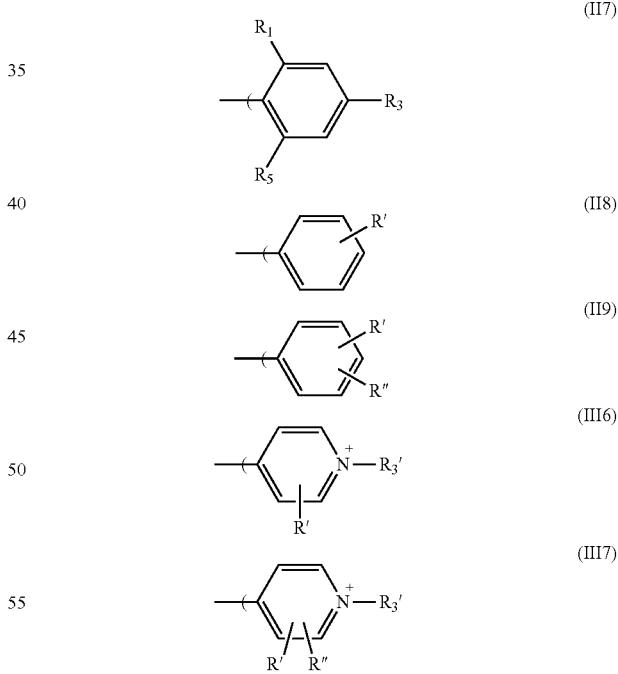

wherein Rd is a $(C_1-C_8)$ alkyl chain, or $-(CH_2)_n SO_3^-$, n being an integer chosen from 1, 2, 3, 4 or 5.

Thanks to the presence of above-mentioned substituents which are hydrophilic, the corroles of this embodiment is also water-soluble.

In a particular embodiment, the corroles of the invention are corroles of type A3, wherein $A_1$ and $A_2$ on the corrole of formula (I) are represented by one formula chosen from formula (II4), formula (II5), formula (II6), formula (III3), formula (III4), formula (III5), or formula (IV3) or a pharmaceutically acceptable salt thereof, or an optical isomer thereof.

In another particular embodiment, the corroles of the invention are corroles of type A2B, wherein $A_1$ and $A_2$ on the corrole of formula (I) are different, $A_2$ being represented by the formula (II4), (II5), (II6), (III3), (III4), (III5), or (IV3) as defined before, $A_1$ being represented by the formula (II7), formula (II8), formula (II9), formula (III6), or formula (III7)

wherein R' and R" represent respectively 2 different substituents among $R_1$, $R_2$, $R_3$, $R_4$ and $R_5$ or 2 different substituents among $R_1'$, $R_2'$, $R_4'$ and $R_5'$; $R_1$, $R_2$, $R_3$, R', R" and $R_3'$ being independently chosen from:

a $(C_1-C_8)$ alkyl chain, a PEG chain of formula $-(CH_2-CH_2-O)_n-H$ or of formula $-(CH_2-CH_2-O)_n-CH_3$, wherein n is an integer chosen from 1, 2, 3, 4 or 5, a group of formula

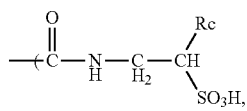

wherein Rc is —COOH, or —SO$_3$H a pyridinium group of formula

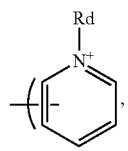

wherein Rd is a (C$_1$-C$_8$) alkyl chain, or —(CH$_2$)$_n$SO$_3^-$, n being an integer chosen from 1, 2, 3, 4 or 5.

According to formula (II8), R' can be any one substituent of R$_1$, R$_2$, R$_3$, R$_4$ and R$_5$, while the other substituents of R$_1$, R$_2$, R$_3$, R$_4$ and R$_5$ are hydrogen.

According to formula (II9), R' and R" represent any two substituents among R$_1$, R$_2$, R$_3$, R$_4$ and R$_5$, while the other three substituents of R$_1$, R$_2$, R$_3$, R$_4$ and R$_5$ are hydrogen.

According to formula (III6), R' can be any one of R$_1$', R$_2$', R$_4$' and R$_5$', while the other three substituents of R$_1$', R$_2$', R$_4$' and R$_5$' are hydrogen.

According to formula (III7), R' and R" can be any two substituents of R$_1$', R$_2$', R$_4$' and R$_5$', while the other two substituents of R$_1$', R$_2$', R$_4$' and R$_5$' are hydrogen.

In another particular embodiment, the corroles of the invention are corroles of type A2B, wherein A$_1$ and A$_2$ on the corroles of formula (I) are different, A$_1$ being represented by the formula (II4), (II5), (II6), (III3), (III4), (III5) as defined above A$_2$ being represented by the formula or (IV3), (II7), (II8), (II9), (III6), or (III7), as defined above.

In a more particular embodiment of the present invention, the corroles are chosen from following compounds:

(A)
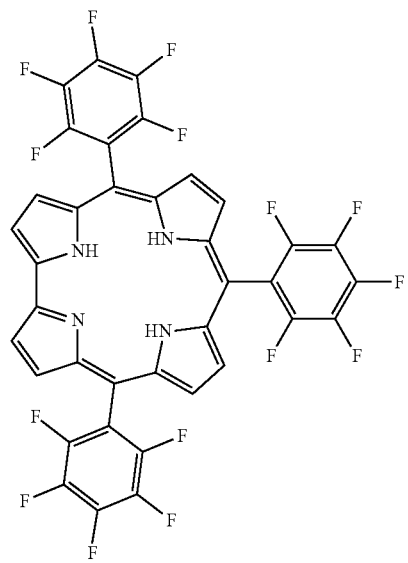

(B)
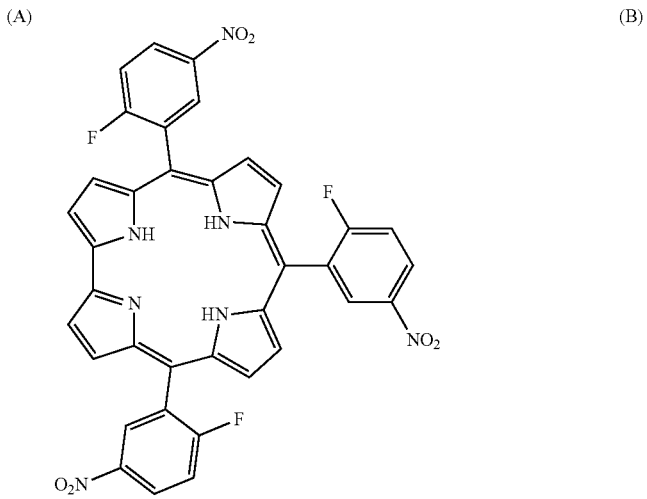

(C)
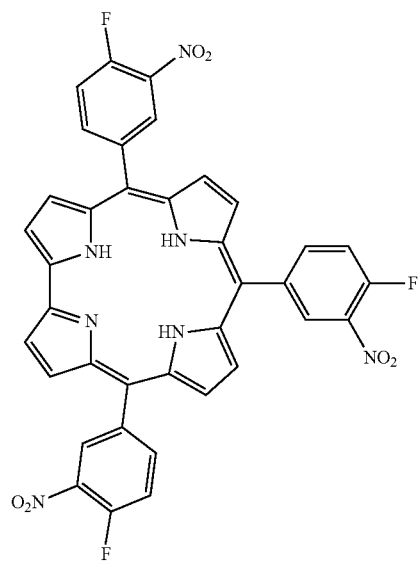

(D)
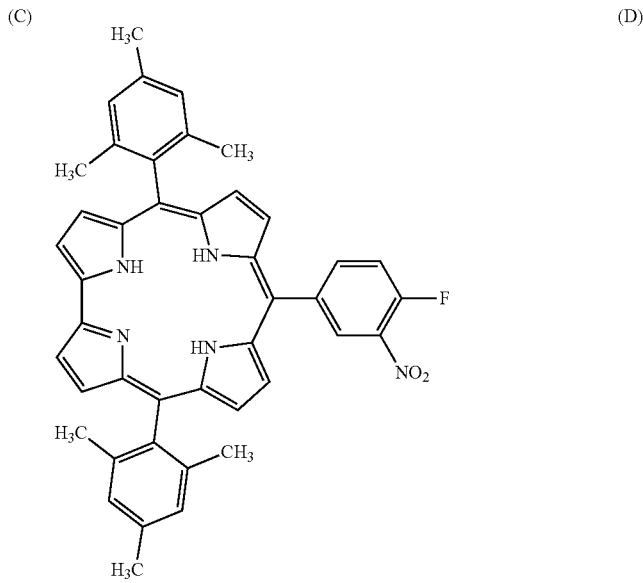

-continued
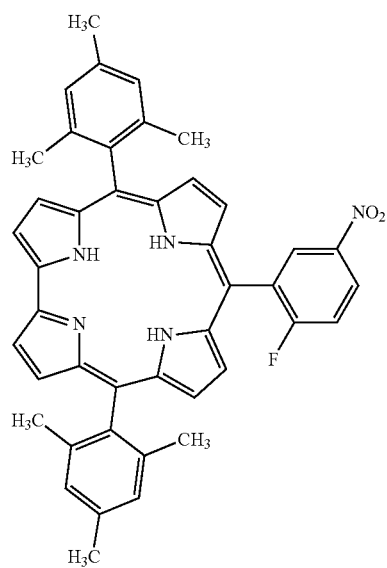
(E)
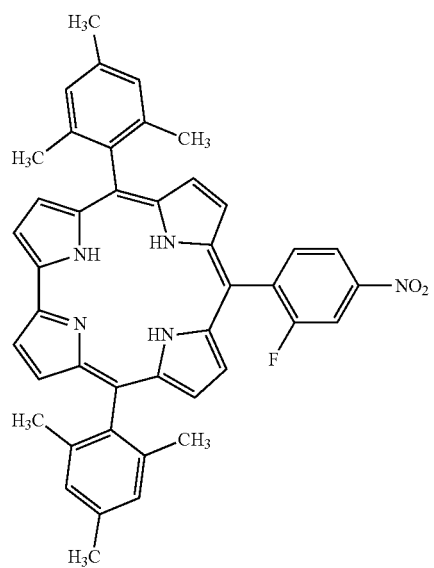
(F)
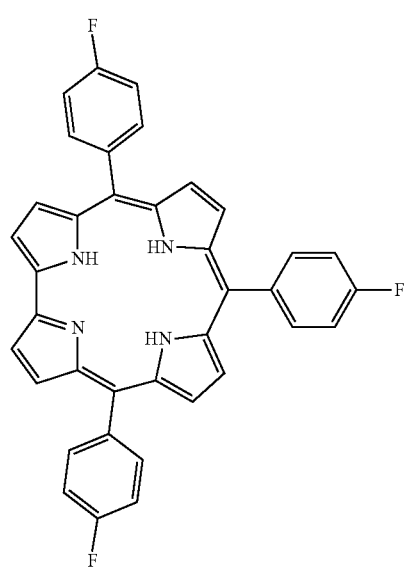
(G)
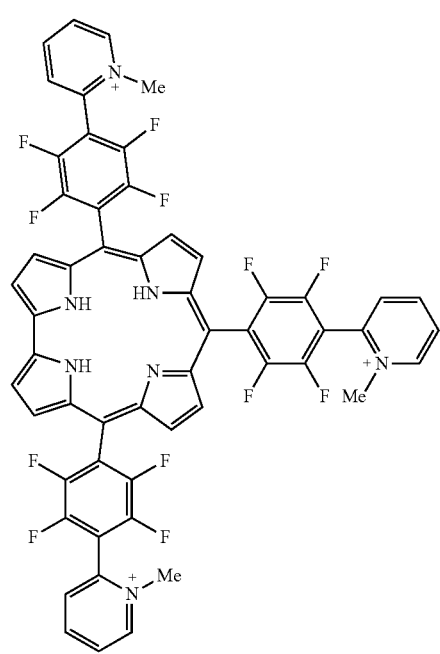
(H)

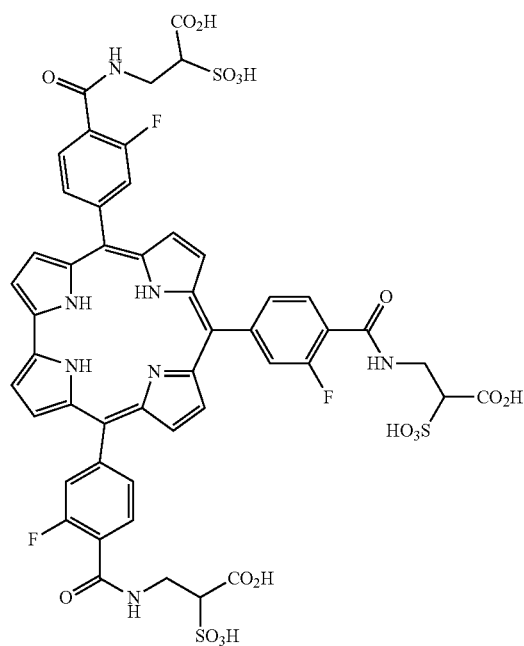
(I)
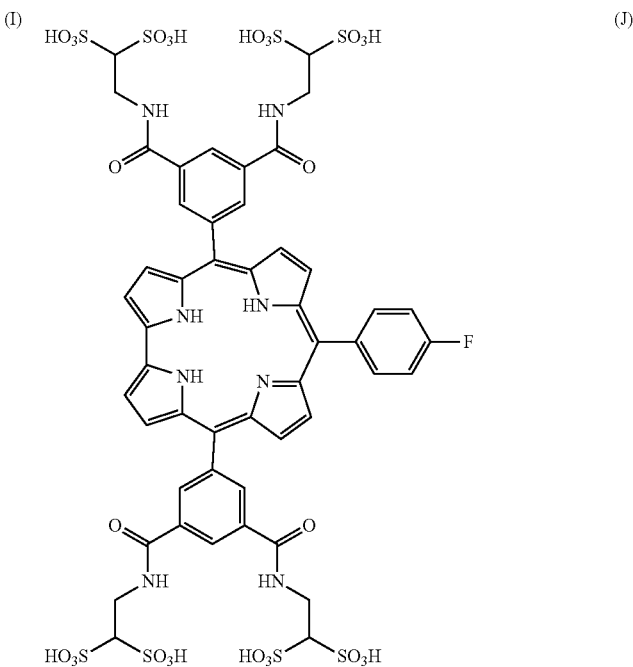
(J)
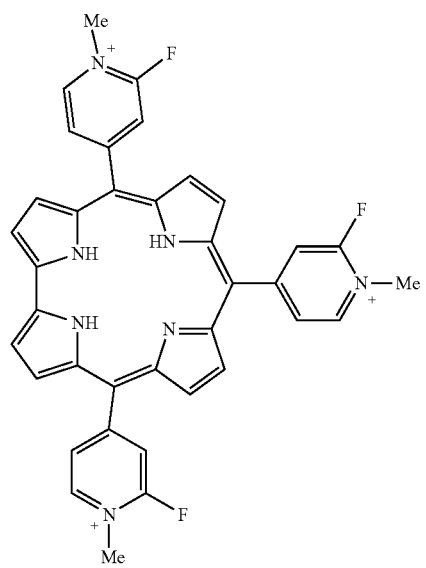
(K)
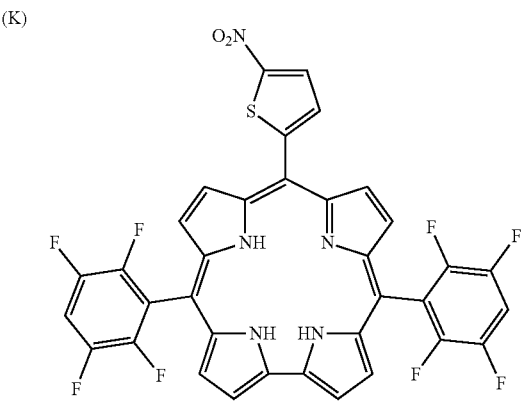
(L)

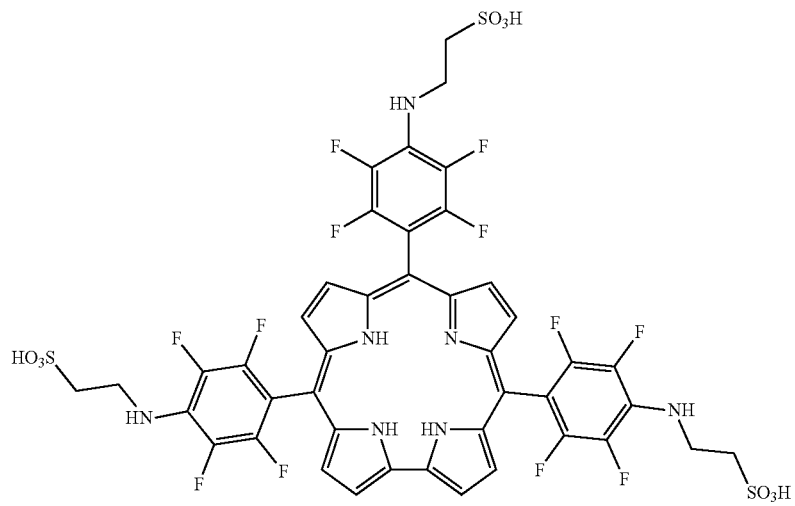

(M)

or a pharmaceutically acceptable salt thereof, or an optical isomer thereof.

In a particular embodiment, the present invention concerns one of the above-mentioned compound A, B, C, D, E, F, G, H, I, J, K, L, M for their use in the treatment of retinitis.

Another subject-matter of the present invention concerns an association formed by:
- a corrole of formula (I) as defined above or a pharmaceutical acceptable salt thereof, or an optical isomer thereof,
- the active ingredient of another anti-hCMV medicament chosen from Ganciclovir, Cidofovir, or Foscarnet, Valganciclovir, Brincidofovir, Letermovir, or any experimental anti-hCMV medicament, for its use in the treatment of an infection of human cytomegalovirus.

In the present invention, the terms "medicament" and "drug" are interchangeable.

The term "active ingredient" is meant to the biologically active component of a medicament.

It is observed that an association of a commercially available anti-hCMV medicament with a corrole of the present invention can produce a synergistic therapeutic effect in treatment of hCMV infection. This synergy may be due to the fact that a corrole of the present invention reacts on hCMV by a very different mechanism of action then that of actually commercially available anti-hCMV drugs, such as Ganciclovir.

In a particular embodiment, the present invention concerns an association formed by:
- a corrole of formula A, B, C, D, E, F, G, H, I, J, K, L or M,
- the active ingredient of Ganciclovir, Cidofovir, Foscarnet, Valganciclovir, Brincidofovir, or Letermovir.

According to an embodiment of said association, the corrole of the present invention is associated to another anti-hCMV active ingredient by a chemical linker. This chemical linker can be in vivo cleavable.

The present invention also relates to a combination product comprising:
- a corrole of formula (I) as defined above or a pharmaceutical acceptable salt thereof, or an optical isomer thereof,
- the active ingredient of another anti-hCMV medicament chosen from Ganciclovir, Cidofovir, or Foscarnet, Valganciclovir, Brincidofovir, Letermovir, or any experimental anti-hCMV treatment for its simultaneous, separate, or sequential use in the treatment of an infection of human cytomegalovirus.

The term "simultaneous use" is meant to be an administration of two active ingredients by the same route and at the same time.

The term "sequential use" is meant to be an administration sequentially on the time of two active ingredients by the same route.

The term "separate use" is meant to be an administration of 2 active ingredients at the same or substantially the same time by different routes.

Another subject-matter of the present invention concerns a pharmaceutical composition for its use in treating an infection of human herpesvirus, in particular of human cytomegalovirus, comprising a corrole of formula (I) as defined above or a pharmaceutically acceptable salt thereof, or an optical isomer thereof, or an association as defined above, or a combination product as defined above, as active ingredient, and a pharmaceutically acceptable carrier.

The term "pharmaceutically acceptable carrier" means a carrier that is useful in preparing a pharmaceutical composition or formulation that is generally safe, non-toxic, and neither biologically nor otherwise undesirable, and includes a carrier that is acceptable for human pharmaceutical use. The carrier can act as a vehicle, medium, or for dilution of the active ingredient. The formulation of the pharmaceutical composition of the present invention can be determined and carried out according to well-known prior art relating to drug formulation. The carrier material can be an organic or inorganic inert carrier material, for example one that is suitable for oral administration or injection. Suitable carriers include water, gelatin, arabic gum, lactose, starch, magnesium stearate, talc, vegetable oils, polyalkylene-glycols, glycerine and petroleum jelly. Additional additives such as flavoring agents, preservatives, stabilizers, emulsifying agents, buffers and the like may be added in accordance with accepted practices of pharmaceutical compounding.

The compositions can be in the form of tablets, pills, powders, lozenges, sachets, cachets, elixirs, suspensions, emulsions, solutions, syrups, soft and hard gelatin capsules, suppositories, sterile injectable solutions, and sterile packaged powders.

According to the formulation, the pharmaceutical composition of the present invention can be administrated by oral route or by injection.

The present invention provides also a method for treating the infections by human cytomegalovirus, such as pneumonitis, esophagitis, gastritis, enterocolitis, retinitis, hepatitis, encephalitis causing by human CMV infection, comprising the step of:

administrating a pharmaceutically effective amount of the aforementioned pharmaceutical composition to a patient suffering from an infection by human cytomegalovirus, such as pneumonitis, esophagitis, gastritis, enterocolitis, retinitis, hepatitis, encephalitis causing by human CMV infection.

The term "pharmaceutically effective amount" means the amount of a before defined corrole or of a before defined combination product as pharmaceutical active in a pharmaceutical composition to produce the desired therapeutic effect.

BRIEF DESCRIPTION OF THE DRAWINGS

The present invention is illustrated by the following figures and examples.

FIGURES

Figure 1:
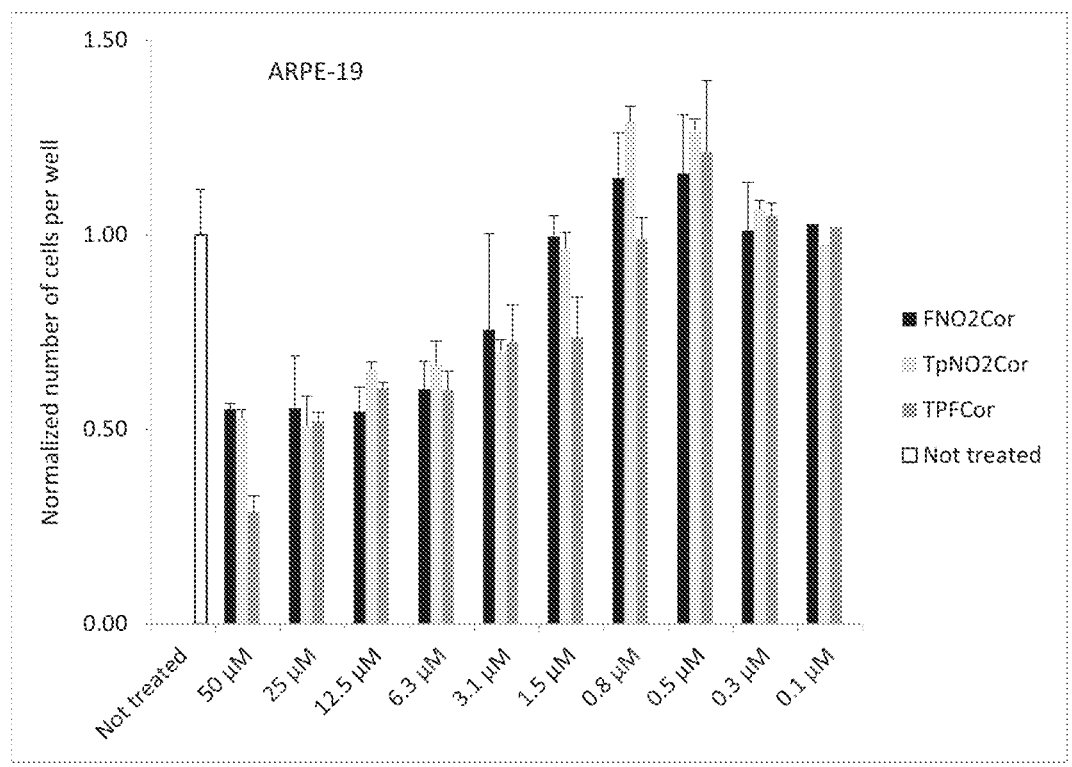

FIG. 1 shows the toxicity of compounds FNO2Cor, TpNO2Cor (positive reference), TPFCor at different concentrations (0.1, 0.25, 0.5, 0.75, 1.5, 3.1, 6.25, 12.5, 25, 50 µM) on ARPE-19 cells seeded on a plate of 96 well. The Y axe shows normalized numbers of survived cells per well.

Figure 2A:
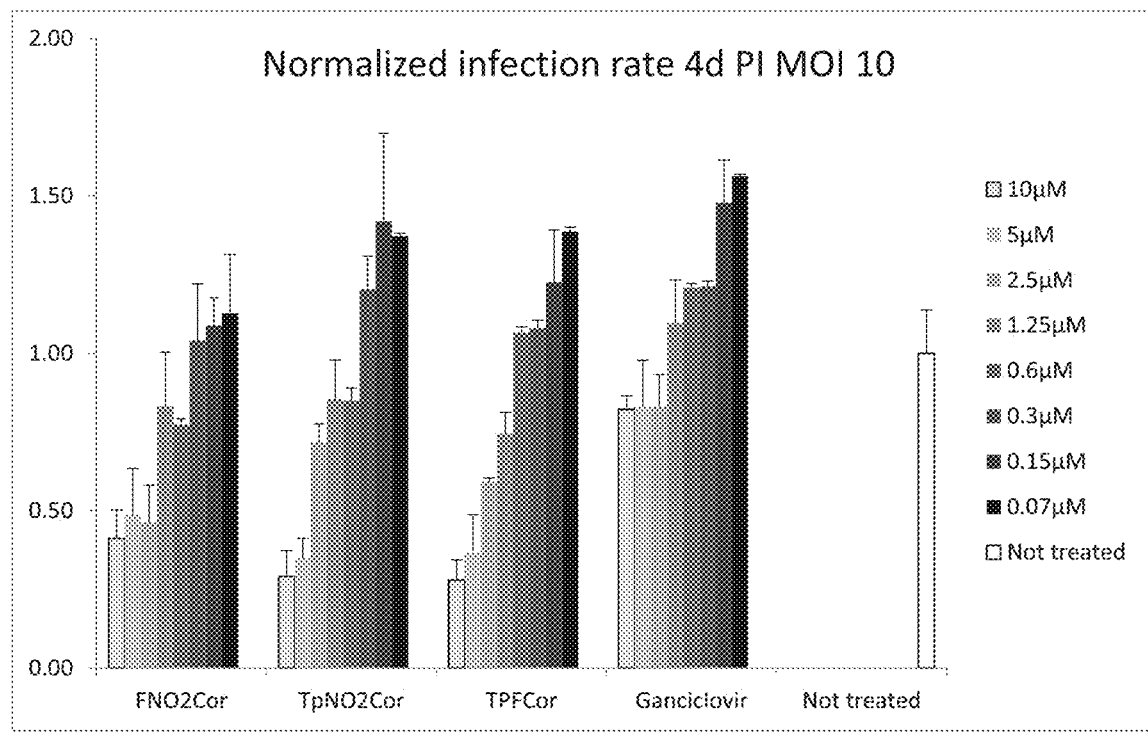
Figure 2B:
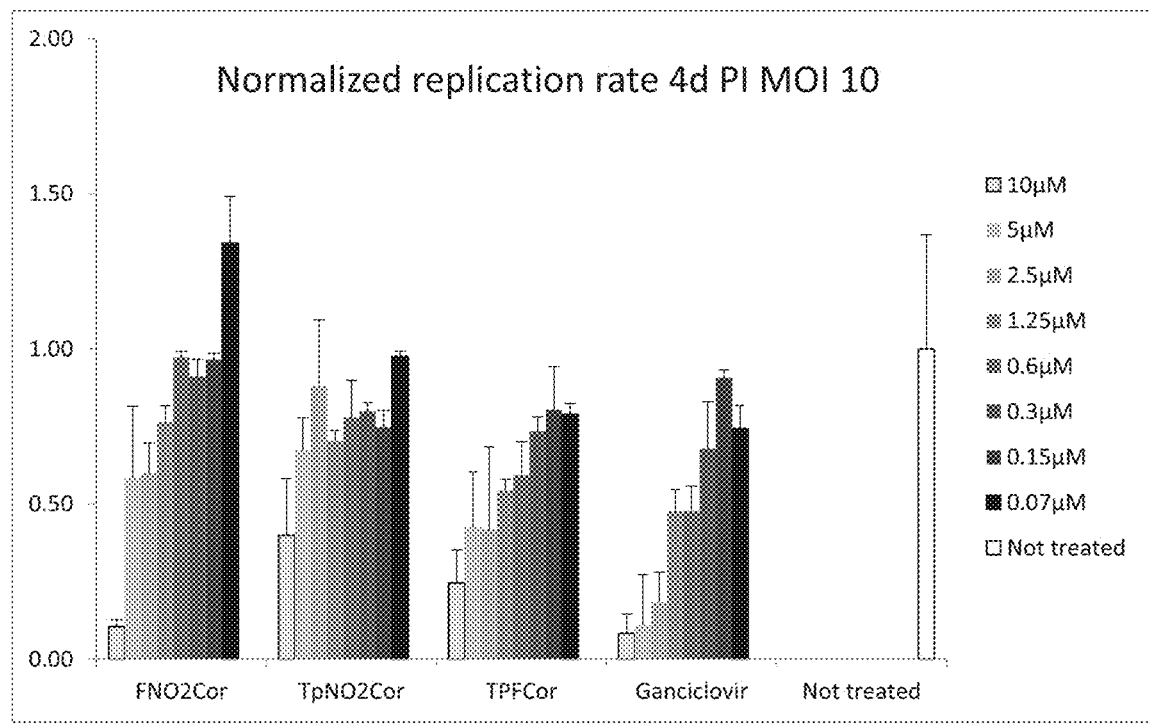

FIGS. 2A and 2B respectively show normalized infection rate (FIG. 2A) of hCMV in ARPE-19 cells and normalized replication rate (FIG. 2B) of hCMV in infected ARPE-19 cells. Cells are treated at MOI (multiplicity of infection) 10 on 4 days post-infection by compounds FNO2Cor, TpNO2Cor, TPFCor, or Ganciclovir at different concentrations (0.07, 0.15, 0.3, 0.6, 1.25, 2.5, 5, 10 µM).

Figure 3A:
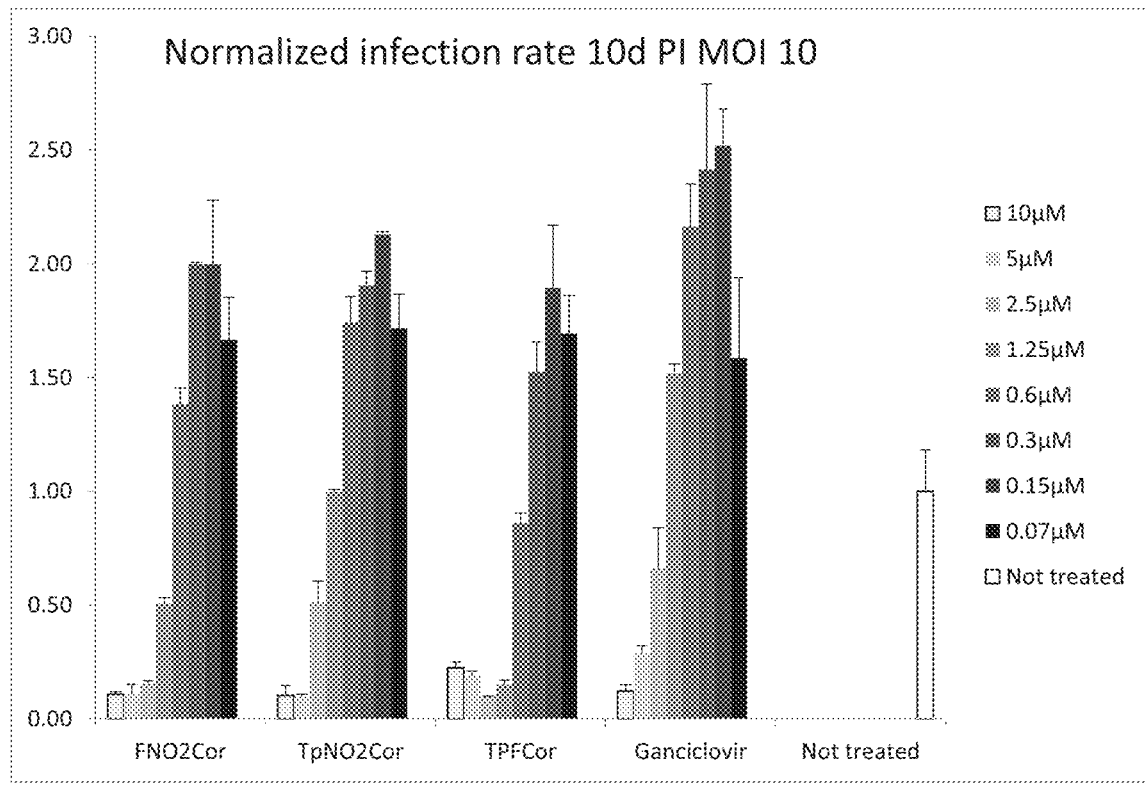
Figure 3B:
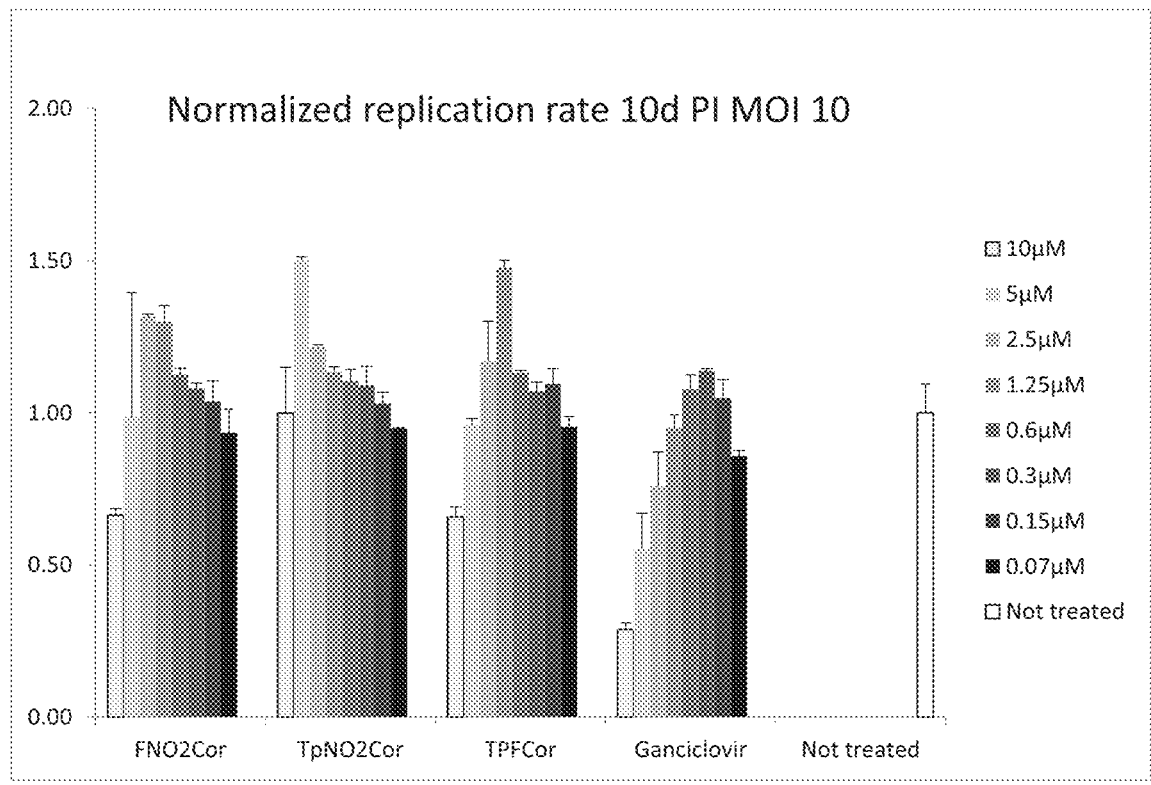
Figure 4A:
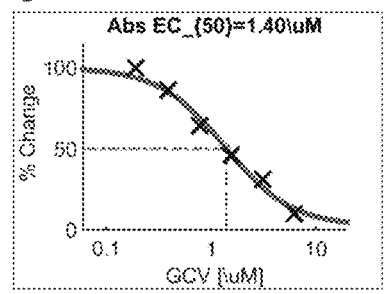
Figure 4B:
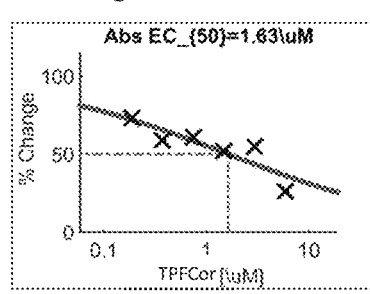
Figure 4C:
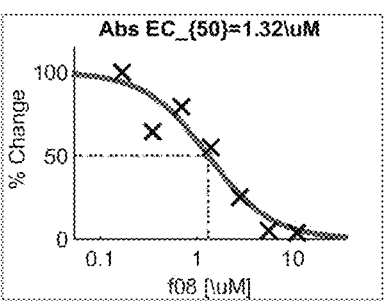
Figure 4D:
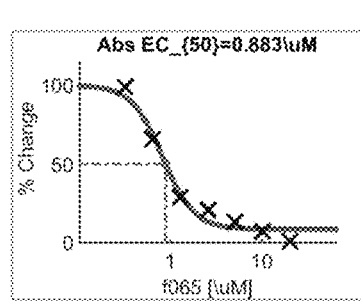
Figure 4E:
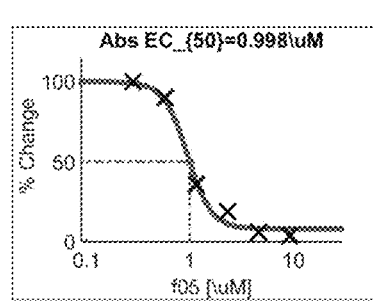
Figure 4F:
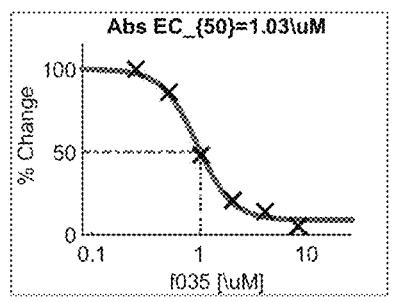
Figure 4G:
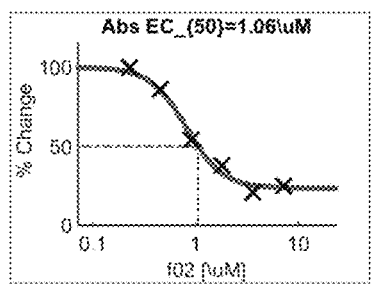

FIGS. 3A and 3B respectively show normalized infection rate (FIG. 3A) of hCMV in ARPE-19 cells and normalized replication rate (FIG. 3B) of hCMV in infected ARPE-19 cells. Cells are treated at MOI (multiplicity of infection) 2 on 10 days post-infection by compounds FNO2Cor, TpNO2Cor, TPFCor, or Ganciclovir at different concentrations (0.07, 0.15, 0.3, 0.6, 1.25, 2.5, 5, 10 µM).

FIGS. 4A, 4B, 4C, 4D, 4E, 4F, 4G respectively show $IC_{50}$ of Ganciclovir alone (FIG. 4A), or of the compound TPFCor alone (FIG. 4B) or of a combination of treatment by Ganciclovir and the compound TPFCor in various ratio (f=0.8 (FIG. 4C), f=0.65 (FIG. 4D), f=0.5 (FIG. 4E), f=0.35 (FIG. 4F), f=0.2 (FIG. 4G)).

DESCRIPTION OF THE PREFERRED EMBODIMENTS

EXAMPLES

1. Materials and Methods
1.1 Preparation of Corroles of the Invention

All the chemical and solvents were of analytical grade and used without any further purification. Silica gel 60 (70-230 and 230-400 mesh, Sigma Aldrich) were used for column chromatography. Reactions were monitored by thin layer chromatography, UV-Vis spectroscopy and mass spectrophotometry. Chromatographic purification on column was performed on silica gel 60 (70-230 mesh, Sigma Aldrich. $^1$H NMR spectra were recorded on a Bruker AV300 spectrometer (300 MHz). $CDCl_3$ was used as solvent (except when indicated) and TMS as internal reference; the chemical shifts (δ) are given in ppm relative to residual $CHCl_3$ (7.26 ppm). All data were processed with TopSpin. MALDI/TOF mass spectra were recorded on Bruker Ultraflex Extreme MALDI Tandem TOF Mass Spectrometer. UV-vis spectra were measured on a Cary 50 spectrophotometer using $CH_2Cl_2$, $CHCl_3$ or THF as solvent.

General procedure #1 according to a modified Paolesse's method (Paolesse et al., *J. Org. Chem.* 2001, 66 (2), 550-556).

Aldehyde (40.4 mmol) and distilled pyrrole (121 mmol) were dissolved in AcOH (500 mL) and the reaction was stirred at reflux for 3 h. The reaction mixture was cooled at room temperature and AcOH was evaporated under vacuum. The crude product was filtered over a chromatography column (silica, $CH_2Cl_2$). All fractions containing corrole (green fraction) were combined and evaporated to dryness. Purification details for each compound are described below.

Preparation of 5,10,15-Tris(4-nitrophenyl)corrole (Designed as TpNO2Cor)

This corrole was prepared as described for general procedure 1 starting from 4-nitrobenzaldehyde and pyrrole. The residue was purified by chromatography column (alumina, $CH_2Cl_2$/heptane, 1/1, v/v) to give pure corrole (492 mg, 5.5%). UV-Vis (DCM): $\lambda_{max}$ (nm) (ε×10$^{-3}$ L mol$^{-1}$ cm$^{-1}$)= 447 (53.4), 598 (18.7). $^1$H NMR (300 MHz, 300 K, DMSO-d6) δ (ppm): 8.41 (m, 2H), 8.58-8.71 (m, 14H), 8.87 (m, 2H), 9.14 (m, 2H). MS (MALDI-TOF) m/z=661.92 [M+H]+, 661.17 calcd for $C_{37}H_{23}N_7O_5$. MS (ESI) m/z=660.15 [M−H]$^-$, 662.14 [M+H]$^+$, 661.17 calcd for $C_{37}H_{23}N_7O_5$.

Preparation of 5,10,15-Tris(2-fluoro-5-nitrophenyl)corrole (designed as FNO2Cor)

This corrole corresponds to the above described compound of formula B. This corrole was prepared as described for general procedure 1 starting from 2-fluoro-5-nitrobenzaldehyde and pyrrole. The residue was crystallized from $CHCl_3$/Heptane (3/1, v/v), separating the solution, containing corrole, from the porphyrin precipitate. Solvent was removed under vacuum and the crude was crystallized from THF/Heptane 1:2 v/v to give pure dark green corrole crystals (76.1 mg, 3.2% yield). UV-Vis (THF): $\lambda_{max}$ (nm) (ε×10$^{-3}$ L mol$^{-1}$ cm$^{-1}$) 418 (103.2), 572, 610, 645. $^1$H NMR (300 MHz, $CDCl_3$), δ (ppm): 9.11-9.00 (m, 5H), 8.73-8.61 (m, 5H), 8.50-8.47 (m, 4H), 7.71-7.62 (m, 3H), −2.83 (brs, 3H). MS (MALDI/TOF): m/z 715.007 [M]$^{+\cdot}$, 715.14 calcd for $C_{37}H_{20}F_3N_7O_6$.

General procedure #2 according to a modified Gryko's method (Gryko, D. T.; Koszarna, B. *Org. Biomol. Chem.*, 2003, 1(2), 350-357).

Aldehyde (20.0 mmol) was dissolved in distilled pyrrole (30.0 mmol) at room temperature and then a solution of TFA in $CH_2Cl_2$ (18 µL in 2.0 mL) was added and vigorously stirred. After 10 min, 800 mL of $CH_2Cl_2$ was added and stirred for further 1 h. DDQ (24.0 mmol) was added and stirred for another 1 h and solvent was removed under vacuum. The crude product was filtered over a chromatography column (silica, $CH_2Cl_2$). Purification details for each compound are described below.

Preparation of
5,10,15-Tris(pentafluorophenyl)corrole (designed as TPFCor)

This corrole correspond to the above described compound of formula A.

This corrole was prepared as described for general procedure 2 starting from pentafluorobenzaldehyde and pyrrole. The residue was purified by a second column chromatography (silica, toluene/heptane, 8/2, v/v) to give pure dark green corrole crystals (228 mg, 4.3% yield). UV-Vis (THF): $\lambda_{max}$, (nm) ($\varepsilon \times 10^{-3}$ L $mol^{-1}$ $cm^{-1}$) 407 (150.1), 562 (23.9), 604 (12.4). $^1$H NMR (300 MHz, $CDCl_3$), $\delta$ (ppm): 9.10 (d, J=4.2 Hz, 2H), 8.79 (d, J=4.8 Hz, 2H), 8.60 (4H), 2.88 (brs, 3H). $^{19}$F NMR (282 MHz, $CDCl_3$) 137.2 (2F), 137.7 (4F), 152.2 (2F), 152.8 (1F), 161.5 (4F), 161.9 (2F). MS (MALDI/TOF): m/z 796.91 $[M+H]^+$, 796.07 calcd for $C_{37}H_{11}F_{15}N_4$.

1.2 hCMV Infection

ARPE-19 human retinal pigmented epithelium cells were used for hCMV infection assay.

Cells were grown in DMEM without phenol red (Sigma-Aldrich) 10% SVF, Pen-strep, 1× sodium pyruvate, 1× Glutamax.

hCMV Infection Protocol hCMV infection was carried out on ARPE-19 cells seeded in 96 wells plate, in duplicate at one or two MOI (multiplicity of infection) and 7 concentrations of FNO2Cor, TPFCor, TpNO2Cor.

D0: MRC5/ARPE-19 cells seeded at 6 k per well in Corning Glass Bottom 96 well plates in 200 μL of DMEM without phenol red.

D1: cells were treated with FNO2Cor, TpNO2Cor, TPFCor (from 50 to 0.1 μM by two fold dilutions) in duplicate for the toxicity study.

D3: ARPE-19 cells were treated with Ganciclovir, FNO2Cor, TpNO2Cor, TPFCor (from 5 to 0.07 μM or from 10 to 0.15 μM by two fold dilutions) and were infected at different MOI in duplicate: MOI 10 or 2 for ARPE-19 cells.

D7: ARPE-19 cells at MOI 10 4 d post-infection were fixed with Formalin 10 min at room temperature. Cells were washed with 200 μL PBS and 100 μL PBS/Hoechst® 33342 (1/1000) per well. 96 well plates were kept at 4° C. in the dark until data acquisition Image acquisition and analysis for high content quantification was performed on a Thermo Cellomics Arrayscan™ VTI microscope using a modified compartmental analysis algorithm.

D13: ARPE19 cells at MOI 2 10 days post-infection were fixed and image acquisition and analysis were performed as previously described.

On 4 d and 10 d post-infection (2 post-infection times), data acquisition per virus and cell line was done by high content microscopy to calculate infection level and DNA replication according to compound concentration.

1.3 Toxicity Assessment

The toxicity of compounds FNO2Cor or TPFCor on ARPE-19 cells was evaluated after 6 days of treatment. 10 concentrations (50, 25, 12.5, 6.25, 3.1, 1.5, 0.75, 0.5, 0.25, 0.1 μM) of FNO2Cor and TPFCor were studied. The compound TpNO2Cor was used as positive control. Cell culture without treatment was used as negative control.

2. Results 2.1 Cytotoxicity

Cytotoxicity of compounds FNO2Cor, TPFCor and TpNO2Cor were assessed at different concentrations on ARPE-19 cells according to the method described on section 1.3. TpNO2Cor worked as positive reference. $CC_{50}$ values of these three compounds on ARPE-19 cells are given in table I below.

TABLE I

|  | FNO2Cor | TpNO2Cor | TPFCor |
| --- | --- | --- | --- |
| $CC_{50}$ ARPE-19 | 50 | 25 | 26.05 |

It is already known that TpNO2Cor is not cytotoxic (Gros et al., 2015). FIG. 1 and Table I show that the cytotoxicity of compound TPFCor is similar to that of TpNO2Cor and compound FNO2Cor has even less cytotoxicity.

These results indicate that FNO2Cor and TPFCor are safe for human retinal pigmented epithelium cells.

2.2 Antiviral Activity

Compounds FNO2Cor, TPFCor, TpNO2Cor and anti-hCMV drug Ganciclovir were assessed at 8 different concentrations in ARPE-19 cell culture on 4 days post-infection (FIGS. 2A, 2B) or on 10 days post-infection (FIGS. 3A, 3B) to evaluate their activity for inhibiting hCMV infection and their capacity for inhibiting hCMV replication in ARPE-19 cells. The results obtained on 4 d PI are displayed in table II. The selectivity index of these compounds on 4 d PI are displayed in table III.

TABLE II

| 4 d PI | FNO2Cor | TpNO2Cor | TPFCor |
| --- | --- | --- | --- |
| IC50 ARPE (infection inhibition) | 2.38 | 3.98 | 3.53 |
| IC50 ARPE (replication inhibition) | 5.92 | 8.34 | 1.6 |

TABLE III

| 4 d PI | FNO2Cor | TpNO2Cor | TPFCor |
| --- | --- | --- | --- |
| Selectivity index (infection inhibition) | 21.05 | 6.28 | 7.38 |
| Selectivity index (replication inhibition) | 8.45 | 3.0 | 16.28 |

These results indicate that the compounds FNO2Cor and TPFCor already have a better selectivity index than that of TpNO2Cor only after 4 d post-infection both for inhibiting hCMV infection of healthy cells and hCMV replication in infected cells.

The results obtained on 10 d PI are displayed below in table IV. The selectivity index of these compounds on 10 d PI are displayed in table V.

TABLE IV

| 10 d PI | FNO2Cor | TpNO2Cor | TPFCor |
| --- | --- | --- | --- |
| IC50 ARPE (infection inhibition) | 1.25 | 1.79 | 0.96 |
| IC50 ARPE (replication inhibition) | 11.78 | nd | 12.27 |

TABLE V

| 4 d PI | FNO2Cor | TpNO2Cor | TPFCor |
|---|---|---|---|
| Selectivity index (infection inhibition) | 39.94 | 13.93 | 27.04 |
| Selectivity index (replication inhibition) | 4.24 | nd | 2.12 |

On 10 d post-infection, the compounds FNO2Cor and TPFCor show significantly much better selectivity index than TpNO2Cor for inhibiting hCMV infection in cells.

2.3 Synergic Antiviral Activity

A combinatory experiment is carried out by using a combination of Ganciclovir and the compound TPFCor.

The experience design is based on Straetemans R et al. (*Biometrical Journal* 47 (2005) 3, 299-308) derived from the Hill model (Hill 1910).

It is based on a ray design, each ray (f) being a combination of the 2 compounds in various ratio (Table VI). The calculation of $IC_{50}$ of each compound alone and of the combination, allows to calculate an interaction index. The results are displayed in FIG. 4.

TABLE VI

| f | Interaction index |
|---|---|
| 0.8 | 0.93 |
| 0.65 | 0.61 |
| 0.5 | 0.68 |
| 0.35 | 0.69 |
| 0.2 | 0.69 |

According to this model an interaction index (Ir) of 1 means additivity, an Ir below 1 means synergy and above 1 antagonism of the two compounds.

The results of FIG. 4 and Table VI show that a combination use of Ganciclovir and a compound of the present application, such as the compound TPFCor produces a synergic antiviral activity.

The invention claimed is:

1. A method for treatment of an infection by human herpes virus chosen from the group comprising cytomegalovirus, herpes simplex virus-1, herpes simplex virus-2, varicella zoster virus, epstein-barr virus, roseolovirus, comprising providing a corrole and administering an effective amount of the corrole, wherein the corrole is of type A3 or A2B of formula (I):

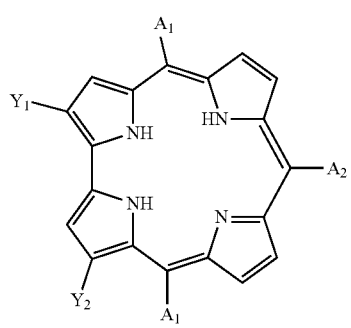

(I)

wherein:

$Y_1$ and $Y_2$ are identical or different and chosen from —H, $A_1$ and $A_2$ are identical or different and each independently represents a phenyl group of formula (II),

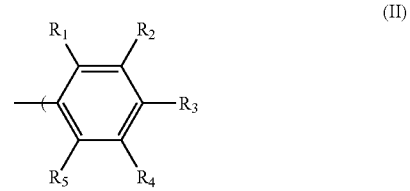

(II)

each of $R_1$, $R_2$, $R_3$, $R_4$ and $R_5$ of formula (II); being chosen independently of each other from:

(a). —H, —NO$_2$, (b). a fluorine atom, wherein at least one of $A_1$ or $A_2$ bears at least one fluorine atom on position $R_1$, $R_2$, $R_3$, $R_4$, $R_5$, or a pharmaceutically acceptable salt thereof, or an optical isomer thereof.

2. The method according to claim 1, wherein $A_1$ and/or A2 are represented by one of formula (II1), (II2) or:

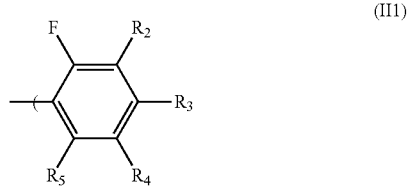

(II1)

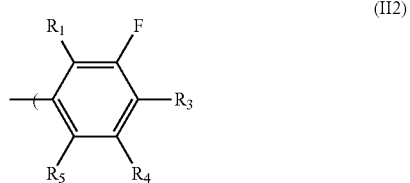

(II2)

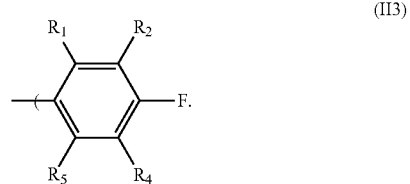

(II3)

3. The method according to claim 2, wherein $A_1$ and/or A2 are represented by one formula chosen from formula (II4), formula (II5), or formula (II6):

(II4)

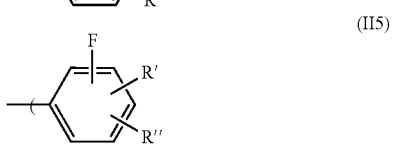

(II5)

-continued

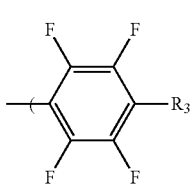
(II6)

wherein R' and R" represent respectively 2 different substituents among $R_1$, $R_2$, $R_3$, $R_4$ and $R_5$.

4. The method according to claim 1, wherein the corrole is chosen from following compounds

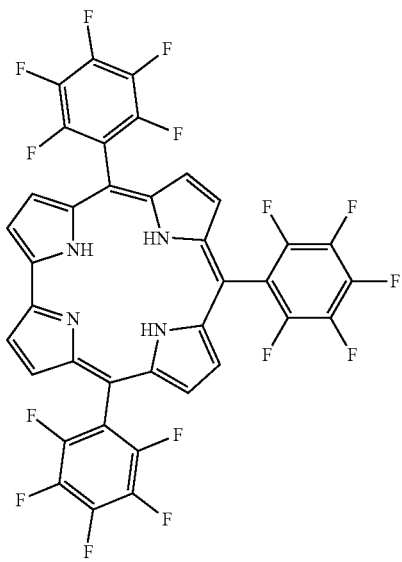
(A)

and

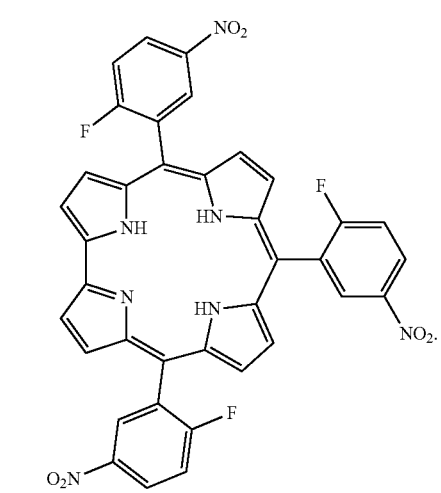
(B)

5. The method according to claim 1, in the treatment of an infection by human cytomegalovirus, said infection being selected from the group comprising pneumonitis, esophagitis, gastritis, enterocolitis, retinitis, hepatitis, encephalitis causing by human CMV infection.

6. The method according to claim 1, in the treatment of an infection of human cytomegalovirus in an immunodeficient patient, a patient receiving organ transplant or in pregnant women.

7. The method of treatment of claim 1 wherein the carrole is linked to another active ingredient of anti-hCMV medicament chosen from Ganciclovir, Cidofovir, or Foscarnet, Valganciclovir, Brincidofovir, Letermovir, or any experimental anti-hCMV medicament.

8. The method according to claim 7, wherein the anti-hCMV medicament is linked to the corrole by a chemical linker.

9. The method according to claim 2, wherein $A_1$ and $A_2$ are different, $A_1$ being represented by the formula (II4), (II5), or (II6):

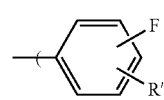
(II4)

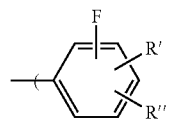
(II5)

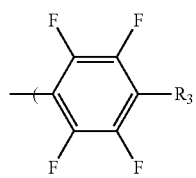
(II6)

$A_2$ being represented by the formula (II7), (II8), or (II9):

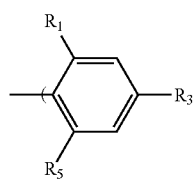
(II7)

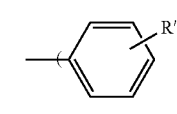
(II8)

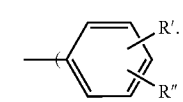
(II9)

10. The method according to claim 3, wherein $A_1$ and $A_2$ are different, $A_1$ being represented by the formula (II4), (II5), or (II6):

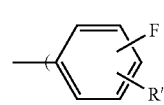
(II4)

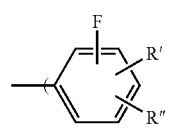
(II5)

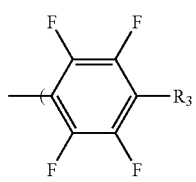
(II6)

$A_2$ being represented by the formula (II7), (II8), or (II9)

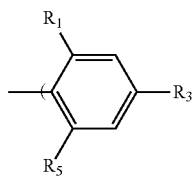
(II7)

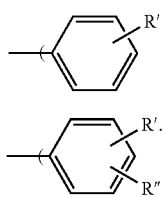
(II8)

(II9)

11. A combination product comprising:
a corrole of as defined in claim 1 or a pharmaceutical acceptable salt thereof, or an optical isomer,
another anti-hCMV medicament chosen from Ganciclovir, Cidofovir, or Foscarnet, Valganciclovir, Brincidofovir, Letermovir, or any experimental anti-hCMV treatment for its simultaneous, separate, or sequential use in the treatment of an infection of human cytomegalovirus.

* * * * *